US00PP18702P2

(12) United States Plant Patent
Austin

(10) Patent No.: US PP18,702 P2
(45) Date of Patent: Apr. 1, 2008

(54) SHRUB ROSE PLANT NAMED 'AUSRELATE'

(50) Latin Name: *Rosa hybrida*
Varietal Denomination: AUSrelate

(75) Inventor: David C. H. Austin, Wolverhampton (GB)

(73) Assignee: David Austin Roses Limited, Albrighton, Wolverhampton (GB)

( * ) Notice: Subject to any disclaimer, the term of this patent is extended or adjusted under 35 U.S.C. 154(b) by 0 days.

(21) Appl. No.: 11/635,429

(22) Filed: Dec. 6, 2006

(51) Int. Cl.
*A01H 5/00* (2006.01)

(52) U.S. Cl. ..... Plt./103

(58) Field of Classification Search ..... Plt./103
See application file for complete search history.

*Primary Examiner*—Kent Bell
*Assistant Examiner*—S. B. McCormick-Ewoldt
(74) *Attorney, Agent, or Firm*—Kauth, Pomeroy, Peck & Bailey LLP

(57) ABSTRACT

Shrub rose plant substantially as herein shown and described, characterized particularly by blooms which start as peachy-pink cupped rosettes and which become domed, creamy-white blooms; a vigorous, well balanced and rounded shrub; and a light fragrance with strong notes of clove.

1 Drawing Sheet

Genus and species: *Rosa hybrida.*
Variety denomination: 'AUSrelate'.

ORIGIN OF THE INVENTION

The present invention relates to a new and distinct variety of a shrub rose plant named 'AUSrelate' which was originated by me by crossing an unnamed, unpatented seedling with an unnamed, unpatented seedling.

BACKGROUND OF THE INVENTION

The primary objective of this breeding was to produce a repeat flowering healthy variety with creamy white blooms on a vigorous shrub.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Blooms which start as peachy-pink cupped rosettes and which become domed, creamy-white blooms.
2. A vigorous, well balanced and rounded shrub.
3. A light fragrance with strong notes of clove.

Asexual reproduction of this new variety by budding, as performed at Albrighton, England, shows that the foregoing and all other characteristics and distinctions come true to form and are established and transmitted through succeeding propagations.

Comparison with Parents

The seed parent has single blooms and grey-green foliage compared with the double blooms and dark green foliage of 'AUSrelate'. The pollen parent has apricot-orange blooms compared with the creamy-white blooms of 'AUSrelate'.

Comparison with Similar Variety

'AUSlevel' (U.S. Plant Pat. No. 8,765) has more petals per bloom than 'AUSrelate' and has larger, less glossy foliage. 'AUSrelate' has a touch of apricot in its creamy-white blooms whereas 'AUSlevel' does not.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—Unnamed Seedling (Unpatented).
*Pollen parent.*—Unnamed Seedling (Unpatented).

FLOWER

Observations made from plants commencing at one year of age grown in a garden environment at Albrighton, England.

Blooming habit: Recurrent. The number of blooms per plant during the growing season is profuse, there are too many to count.

Bud:
*Size.*—About 3 cm long and 2 cm in diameter when the petals start to unfurl.
*Form.*—The bud form is pointed ovoid.

*Color.*—When sepals first divide, bud color is Greyed-Yellow Group 160C with patches of Red Group 53B. When half blown, the upper sides of the petals are White Group 155A and the lower sides of the petals are Yellow Group 11D.

*Sepals.*—Color: Upper surface: Yellow-Green Group 147C overlaid with Greyed-Purple Group 183D toward the tip. Lower surface: Yellow-Green Group 144A. Length: 2.5 cm. Width: 1.0 cm. Shape: Subulate. Surface texture: Upper surface: Pubescent. Lower surface: Smooth. There are three lightly appendaged sepals. There are two unappendaged sepals with canescent edges.

*Receptacle.*—Color: Yellow-Green Group 144A. Shape: Campanulate. Size: Medium, about 1.0 cm long×1.0 cm wide. Surface: Smooth.

*Peduncle.*—Length: Medium, averaging about 6 cm. Surface: Glandular. Color: Yellow-Green Group 144A with a touch of Greyed-Purple Group 187A before the bud unfurls. Strength: Weak.

Bloom:

*Size.*—Large. Average open diameter is about 8.6 cm.

*Borne.*—Several together in irregular compound corymb clusters of about four to five blooms.

*Stems.*—Strength: Strong. Average length is about 30 cm with a diameter of about 0.6 cm.

*Form.*—When first open: Cupped. Permanence: Outer petals curl back.

*Petalage.*—Number of petals under normal conditions: 95-100.

*Color.*—The upper sides of the petals are Yellow-White Group 158B. The reverse sides of the petals are Yellow Group 8D. The base of each petal is Yellow Group 8A. Petals are susceptible to spotting from rain/water which shows as pink spotting on the reverse of the outer petals.

*Variegations.*—None.

*Discoloration.*—The general tonality at the end of the first day is Yellow-White Group 158B. At the end of the third day: White Group 155A.

*Fragrance.*—Slight, fruity with occasional strong hints of clove.

Petals:

*Texture.*—Smooth.

*Size.*—Width: 2.7 cm. Length: 4.0 cm.

*Surface.*—Smooth.

*Shape.*—Obovate. Margin: Entire, some slightly notched. Apex Shape: Obtuse, a few are cuspidate. Base Shape: Cuneate. Form: Incurved.

*Arrangement.*—Imbricated.

*Petaloids.*—Number: None.

*Persistence.*—Petals drop off cleanly before drying.

*Lastingness.*—On the plant: Fair (about 4 days). As a cut flower: Fair (about 4 days).

Reproductive parts:

*Stamens.*—Number: 55. Length: 10 mm. Anthers: Length: 2 mm. Color: Yellow-Orange Group 16A. Arrangement: Regular around styles. Filaments: Color: Yellow Group 8A. Length: 8 mm. Pollen: Color: Yellow-Orange Group 16A.

*Pistils.*—Number: 55. Length: 9 mm. Styles: Color: Green-Yellow Group 1C. Length: 8 mm. Stigmas: Color: Yellow Group 2C. Length: 1 mm.

*Hips.*—None observed.

PLANT

*Form.*—Shrub.

*Growth.*—Vigorous.

*Age at maturity.*—Two years.

*Mature plant.*—Height: 1.2 m. Width: 1.0 m.

*Rootstock.*—'Dr. Huey' in the USA. *Rosa dumetorum* 'Laxa' for the observed plants in the U.K.

Foliage: Number of leaflets on normal mid-stem leaves: 5 or 7 (including terminal leaflet).

*Size.*—Medium. About 14.8 cm long×12 cm wide.

*Quantity.*—Normal. Average number leaves per flowering stem: 10.

*Color.*—New foliage: Upper side: Yellow-Green Group 146A with Greyed-Purple Group 183C concentrated around margin. Lower side: Yellow-Green Group 146C overlaid with Greyed-Purple Group 183C. Old foliage: Upper side: Yellow-Green Group 147A. Lower side: Green Group 137C.

Leaflets:

*Size.*—About 6.9 cm long×4.4 cm wide.

*Shape.*—Pointed oval.

*Base shape.*—Rounded.

*Apex shape.*—Acuminate.

*Texture.*—Smooth, semi-glossy.

*Edge.*—Serrated.

*Serrations.*—Single, large.

*Petiole.*—Color: Yellow-Green Group 144C. Length: 3.5 cm. Width: 2 mm. Surface texture: Smooth.

*Petiole rachis.*—Color: Yellow-Green Group 144C. Underside: With prickles.

*Stipules.*—Length: 2 cm; erose and glandular. Color: Yellow-Green Group 144A.

*Auricle shape.*—Subulate. Length: 5 mm. Width: 2 mm, tapering to a point. Color: Yellow-Green Group 144A.

*Disease resistance.*—Resistant to powdery and downy mildew, blackspot and rust in normal growing conditions.

*Pest resistance.*—Not tested.

*Vein color.*—Yellow-Green Group 145C.

*Venation pattern.*—Reticulate.

Wood:

*New wood.*—Color: Yellow-Green Group 144A. Bark: Smooth.

*Old wood.*—Color: Yellow-Green Group 144A. Bark: Smooth.

Stems:

*Mature stem.*—Length: 30 cm. Diameter: 6 mm.

*Internode distance.*—6 cm. The above measurements are all variable, depending on growing conditions in a season.

Prickles:

*Quantity.*—On main canes from base: Few, 5 per 10 cm stem length. On laterals from main canes: Few, 5 per 10 cm per stem length.

*Form.*—Concave curved inward.

*Length.*—6 mm.

*Color when young.*—Greyed-Red Group 181A.

*Color when mature.*—Greyed-Red Group 181A.

Small prickles:

*Quantity.*—On main stalks: None. On laterals: None.

Winter hardiness: Not tested.

I claim:

1. A new and distinct variety of shrub rose plant substantially as herein shown and described, characterized particularly by blooms which start as peachy-pink cupped rosettes and which become domed, creamy-white blooms; a vigorous, well balanced and rounded shrub; and a light fragrance with strong notes of clove.

* * * * *

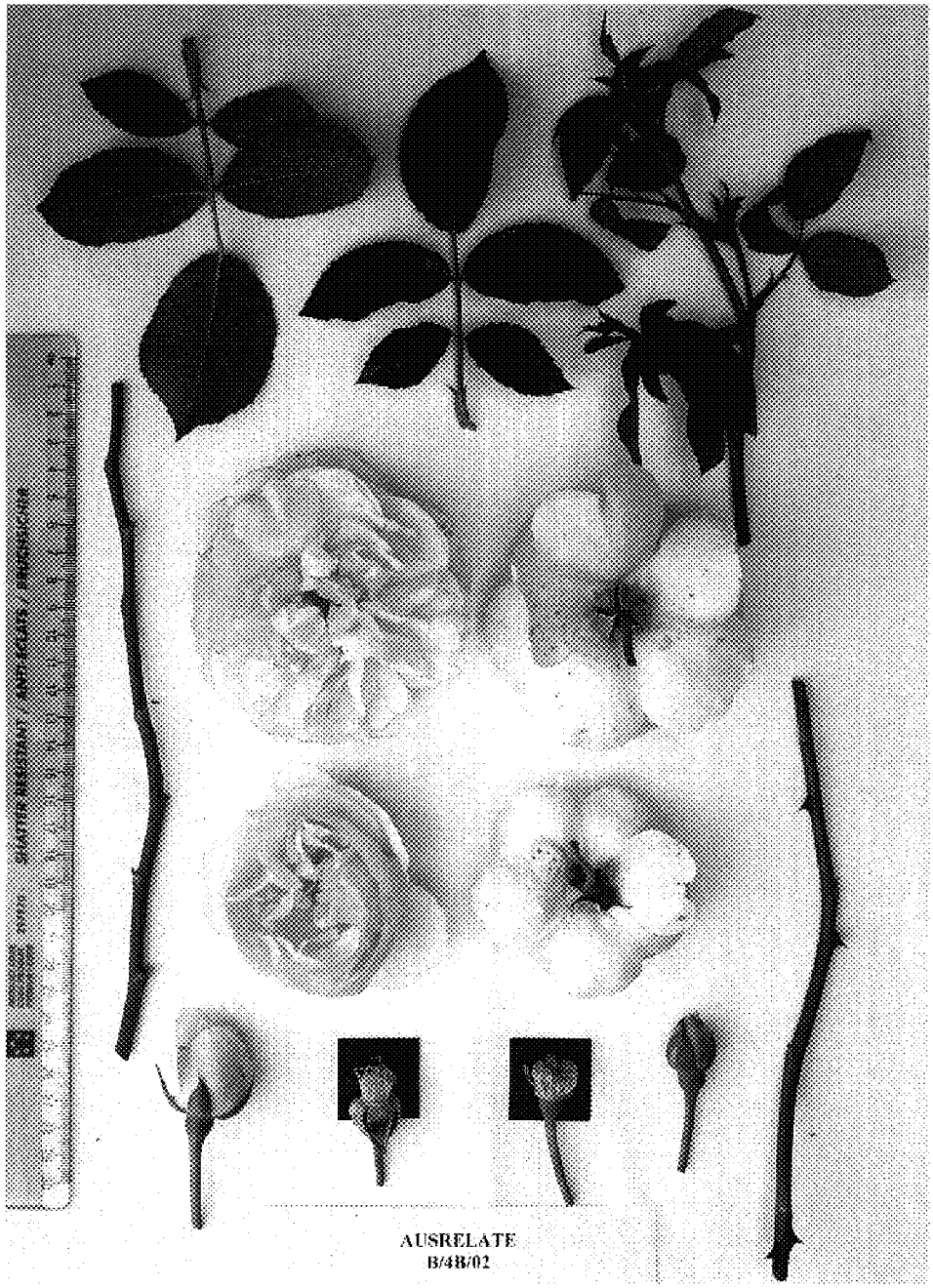
AUSRELATE
B/4B/02